United States Patent
Belthangady et al.

(10) Patent No.: US 11,096,586 B1
(45) Date of Patent: Aug. 24, 2021

(54) SYSTEMS FOR DETECTING CARIOUS LESIONS IN TEETH USING SHORT-WAVE INFRARED LIGHT

(71) Applicant: Verily Life Sciences LLC, South San Francisco, CA (US)

(72) Inventors: Chinmay Belthangady, San Francisco, CA (US); Tamara Troy, San Francisco, CA (US); Supriyo Sinha, Menlo Park, CA (US); Daniele Piponi, Oakland, CA (US); Eden Rephaeli, Oakland, CA (US); Seung Ah Lee, San Francisco, CA (US); Maximilian Kapczynski, Palo Alto, CA (US)

(73) Assignee: VERILY LIFE SCIENCES LLC, South San Francisco, CA (US)

(*) Notice: Subject to any disclaimer, the term of this patent is extended or adjusted under 35 U.S.C. 154(b) by 16 days.

(21) Appl. No.: 16/210,288

(22) Filed: Dec. 5, 2018

Related U.S. Application Data

(60) Provisional application No. 62/596,595, filed on Dec. 8, 2017.

(51) Int. Cl.
*G01J 3/06* (2006.01)
*A61B 5/00* (2006.01)

(52) U.S. Cl.
CPC .......... *A61B 5/0088* (2013.01); *A61B 5/0086* (2013.01); *A61B 2562/146* (2013.01); *A61B 2576/02* (2013.01)

(58) Field of Classification Search
CPC .... G01J 5/00; H04N 5/30; H04N 5/33; A61B 5/0088; A61B 5/0086; A61B 2562/146; A61B 2576/02
See application file for complete search history.

(56) References Cited

U.S. PATENT DOCUMENTS

| 9,414,750 B2 | 8/2016 | Lovely |
| 9,500,635 B2 | 11/2016 | Islam |

(Continued)

OTHER PUBLICATIONS

Burmen, M. et al., "A Construction of Standardized Near Infrared Hyper-Spectral Teeth Database—A First Step in the Development of Reliable Diagnostic Tool for Quantification and Early Detection of caries", Proc. of SPIE vol. 7884, 2011, 10 pages.

(Continued)

*Primary Examiner* — David P Porta
*Assistant Examiner* — Mamadou Faye
(74) *Attorney, Agent, or Firm* — Christensen O'Connor Johnson Kindness PLLC

(57) ABSTRACT

Systems, apparatuses, and methods for detecting carious lesions are described herein. In an example, the systems in an optical interrogator including a single-pixel photodetector responsive to short-wave infrared light and operatively coupled to a controller. In an example the optical interrogator includes a plurality of lasers for emitting laser light, a scanning mirror assembly and a single-pixel photodetector. In an example, the methods include causing the plurality of lasers to emit the laser light having wavelengths in a range of about 900 nm to about 1,700 nm; selectively directing the laser light over different portions of a tooth with a scanning mirror assembly to provide scattered light; and correlating scattered light signals generated by the single-pixel photodetector in response to the scattered light with the portion of the tooth.

16 Claims, 7 Drawing Sheets

(56) References Cited

U.S. PATENT DOCUMENTS

| | | | |
|---|---|---|---|
| 9,510,757 B2 | 12/2016 | Kopelman et al. | |
| 2007/0134615 A1* | 6/2007 | Lovely | A61B 5/0086 433/29 |
| 2009/0053667 A1 | 2/2009 | Chen | |
| 2010/0165335 A1* | 7/2010 | Tearney | G01J 3/02 356/301 |
| 2012/0321759 A1* | 12/2012 | Marinkovich | A61B 5/0531 426/231 |
| 2015/0305627 A1* | 10/2015 | Islam | A61B 5/0022 433/27 |
| 2017/0350759 A1* | 12/2017 | Azumi | G01J 3/0264 |
| 2018/0136344 A1* | 5/2018 | Nelson | A61B 6/4233 |

OTHER PUBLICATIONS

Chung, S. et a;. Near Infrared Imagining of Teeth at Wavelengths Between 1200 and 1600 nm:, Proc. SPIE Int Opt Eng. vol. 7884, Jan. 1, 2011, 11 pages.

Sowa, M. et al., "A Comparison of Methods Using Optical Coherence Tomography to Detect Demineralized Regios in Teeth", J Biophotonics vol. 4, Nov. 2011, pp. 814-823.

\* cited by examiner

SYSTEMS FOR DETECTING CARIOUS LESIONS IN TEETH USING SHORT-WAVE INFRARED LIGHT

CROSS-REFERENCE(S) TO RELATED APPLICATIONS

This application claims the benefit of U.S. Provisional Application No. 62/596,595, filed Dec. 8, 2017, which is hereby incorporated by reference in its entirety.

TECHNICAL FIELD

This disclosure relates generally to systems, apparatuses, and methods for the detection of carious lesions, and in particular but not exclusively, relates to detection of carious lesions using laser light.

BACKGROUND INFORMATION

A carious lesion is the appearance of a chalky white spot on the surface of a tooth, indicating an area of demineralization of tooth enamel. Incidence of dental caries in the US is approximately 92%, with greater than 180 million people between the ages 20-64 years having one or more carious lesions. Worldwide incidence of dental caries is close to 100%.

If left untreated, a carious lesion can develop into a dental cavity. Further, when *Streptococcus mutans*, the primary bacterium responsible for tooth decay, gains access to the bloodstream through a carious lesion it can affect systemic health with complications including cardiovascular disease due to bacterially-formed atheromatous plaque.

However, if detected early, the demineralization process is potentially curable and preventable through, for example, fluoride treatment, anti-bacterial therapy, diet, and/or laser irradiation. Accordingly, there is a need for systems and methods for detection of carious lesions.

BRIEF DESCRIPTION OF THE DRAWINGS

Non-limiting and non-exhaustive embodiments of the claimed subject matter are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

FIG. 5A is a visual-light image of two teeth.

FIG. 5B is a short-wave infrared light image of the two teeth of FIG. 5A.

DETAILED DESCRIPTION

Embodiments of a system, an apparatus, and a method for detection of carious lesions are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Figure 1:
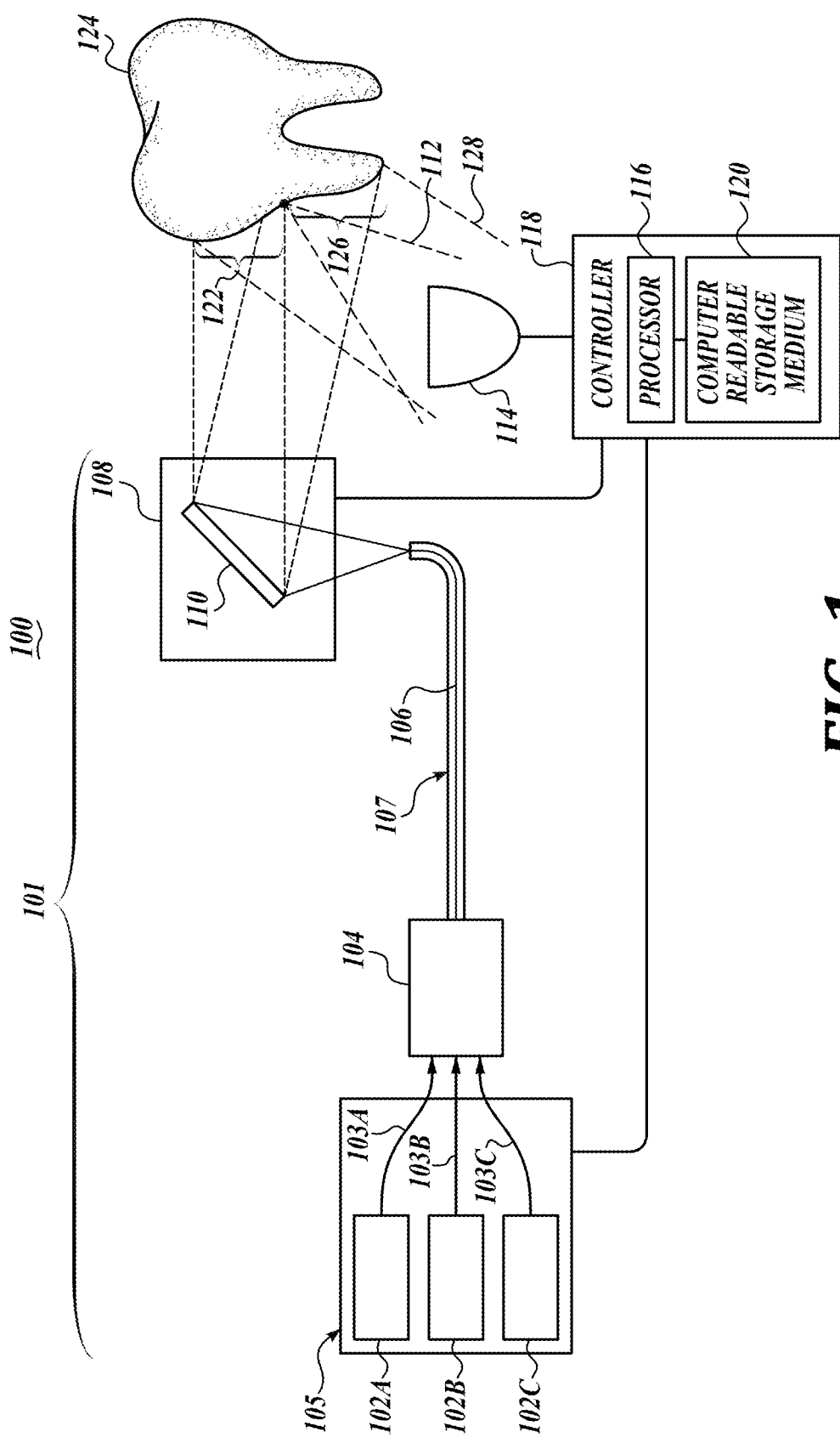
FIG. 1 illustrates a system for detecting carious lesions, in accordance with an embodiment of the disclosure.

FIG. 1 illustrates a system for detecting carious lesions, in accordance with an embodiment of the disclosure. The illustrated embodiment of the system 100 includes an optical interrogator 101 and a controller 118 operatively coupled to the optical interrogator 101. As shown, the optical interrogator 101 includes a laser light engine 105; a wavelength division multiplexer 104 coupled with the laser light engine 105; a scanning assembly 108; and a single-pixel photodetector 114. The laser light engine 105 includes a plurality of lasers 102A, 102B, and 102C for emitting laser light. The wavelength division multiplexer 104 is coupled with the laser light engine 105 to combine at least a portion of laser light 103A, 103B, and 103C emitted by the plurality of lasers 102A, 102B, and 102C, respectively, to provide a combined light beam 106.

In an embodiment, the combined light beam 106 is directed by optical fiber 107 to the scanning assembly 108. Scanning assembly 108 is positioned to reflect the combined light beam 106. In the illustrated embodiment, scanning assembly 108 is a scanning mirror assembly 108. The scanning mirror assembly 108 includes a micro-electromechanical system 110 for selectively altering an orientation of the scanning mirror assembly 108. As shown, the micro-electromechanical system 110 selectively directs the combined light beam 106 onto a portion 122 of a tooth 124. As discussed further herein, the scanning mirror assembly 108 including, in certain embodiments, micro-electromechanical system 110 is used in scanning the combined light beam 106 over different portions of the tooth 124 through altering an orientation of the scanning mirror assembly 108. System 100 includes a photodetector 114 for detecting laser light emitted from laser light engine 105 and scattered off of one or more portions of the tooth 124.

In teeth, the penetration depth of short-wave infrared (SWIR) light is higher than visible light (400-700 nm) due to reduced absorption and lower photon scattering losses of SWIR light when it impinges upon a tooth. In a carious lesion, the increased porosity of the enamel leads to higher photon scatter and the lesion appears as a bright region against the dark background of the sound enamel, especially in the region of high water absorption between 1,400-1,700 nm. As described further herein, this contrast between carious lesions and areas of intact enamel can be used for detection of carious lesions.

Conventional silicon-based complementary metal-oxide-semiconductor (CMOS) cameras are not sensitive to light above 1000 nm. For imaging in the SWIR spectral region, indium-gallium-arsenide (InGaAs) and other SWIR-absorbing cameras can be used. Due to the complexity of the fabrication process, where the SWIR-photosensitive pixel array, such as an InGaAs pixel array, has to be bonded to silicon-CMOS readout electronics, such cameras tend to be much more expensive than their visible-light counterparts. There are also problems related to dead pixels and spatial non-uniformity of the signal across the sensor area.

Accordingly, system 100 includes a SWIR-absorbing single-pixel photodetector 114. In an embodiment, the system 100 includes a single-pixel InGaAs photodetector for absorbing SWIR light. Of course, other SWIR-absorbing single-pixel photodetectors can also be used. As used herein, a single-pixel photodetector refers to a photodetector having only a single photodiode. This is in contrast to a multi-pixel array having two or more photodiode pixels. In an embodiment, the single-pixel photodetector includes a PIN diode. In an embodiment, the single-pixel photodetector includes an avalanche photodiode. Of course, other photodetecting technologies capable of imaging in the SWIR spectrum may also be used.

As illustrated, at least a portion of the scattered light 112 scattered off of the portion 122 of the tooth 124 impinges on and is absorbed by the single-pixel photodetector 114. As discussed further herein, the single-pixel photodetector 114 is configured to generate one or more signals responsive to absorbing infrared light, such as scattered light, absorbed by the single-pixel photodetector 114.

Controller 118 includes logic that, upon execution by the controller 118, causes the system to perform a number of operations. Controller 118 may include a microprocessor for executing software/firmware instructions stored in a memory coupled to the microprocessor, such as processor 116. Alternatively, controller 118 may include hardware logic (e.g., application specific integrated circuit, field programmable gate array, etc.). In yet another embodiment, controller 118 may include a combination of both software logic and hardware logic.

In the illustrated embodiment, controller 118 is coupled to laser light engine 105. In an embodiment, the operations include causing the laser light engine 105 to emit laser light 103A, 103B, and 103C having wavelengths in a range of about 900 nm to about 1,700 nm. In an embodiment, the operations include causing the laser light engine 105 to emit laser light 103A, 103B, and 103C having wavelengths in a range of about 1,400 nm to about 1,700 nm. As discussed further herein, causing the laser light engine 105 to emit laser light 103A, 103B, and 103C having wavelengths in a range of about 900 nm to about 1,700 nm provides light scattered off of a portion 122 of the tooth 124 for absorption by the single-pixel photodetector 114.

In an embodiment, one or more of the plurality of lasers 102A, 102B, and 102C emit laser light 103A, 103B, and 103C, respectively, that has a different emission spectrum than the laser light of the other lasers of the plurality of lasers. As discussed further herein, in an embodiment, the relative emission intensity of the laser light 103A-103C emitted by lasers 102A, 102B, and 102C of the plurality of lasers is configured to enhance contrast in signals generated by the single-pixel photodetector 114 in response to absorbing scattered light 112 scattered off of carious lesions, on the one hand, and areas of intact enamel on the other. Accordingly, in an embodiment, the operations include causing one of the lasers 102A-102C to emit laser light 103A-103C, respectively, at an emission intensity greater than the intensity of one or more of the lasers of the laser light engine 105.

Controller 118 is coupled to scanning mirror assembly 108 and the single-pixel photodetector 114. In an embodiment, the operations include selectively directing the combined light beam 106 to a portion 122 of the tooth 124 with the scanning mirror assembly 108 and correlating scattered light signals generated by the single-pixel photodetector 114 in response to scattered light 112 scattered off of the portion 122 of the tooth 124 and the portion 122 of the tooth 124. Selectively directing the combined light beam 106 to a portion 122 of the tooth 124 with the scanning mirror assembly 108 includes operating one or more actuators in the scanning mirror assembly 108 to alter an orientation of the scanning mirror assembly 108, thereby altering a direction of the combined light beam 106.

In an embodiment, the portion 122 of the tooth 124 is a first portion of the tooth 124 and the operations further include sequentially and selectively directing the combined light beam 106 to a second portion 126 of the tooth, different from the first portion of the tooth 122, with the scanning mirror assembly 108 and correlating one or more second scattered light signals generated by the single-pixel photodetector 114 in response to absorbing at least a portion of light 128 scattered off of the second portion 126 of the tooth 124 and the second portion 126 of the tooth 124. Likewise, the operations can include selectively directing the combined light beam 106 sequentially over a plurality of different portions of the tooth 124 with the scanning mirror assembly 108 to provide scattered light 112; and correlating scattered light signals generated by the single-pixel photodetector 114 in response to the scattered light 112 and the plurality portions of the tooth 124. In this regard, the system 100 is configured to inspect a number of portions of the tooth 124 for carious lesions by rastering or otherwise systematically directing the combined light beam 106 onto the portions of the tooth 124 and correlating scattered light signals generated by the single-pixel photodetector 114 in response to absorbing at least a portion of scattered light 112 scattered off of the plurality of portions of the tooth 124 and the respective portions of the tooth 124.

Correlating scattered light signals with different portions of the tooth 124 can include associating a value of a scattered light signal, such as a scattering intensity, and the portion of the tooth 124 that generated the scattered light 112 that gave rise to the scattered light signal. In an embodiment, correlating scattered light signals with different portions of the tooth 124 includes creating a data structure, such as a table, associating the scattered light signals with the respective portions of the tooth that generated them. In an embodiment, correlating scattered light signals with different portions of the tooth 124 includes generating a map of the tooth 124 representing the scattered light signals and the respective portions of the tooth 124.

Controller 118 is operatively coupled to the optical interrogator 101 by one or more of a wired connection or a wireless connection. In some embodiments, the wireless connection is a direct wireless connection, such as a Bluetooth connection, a near field communication (NFC) connection, a direct WiFi connection, or any other direct wireless connection. In some embodiments, the wireless connection is an indirect connection via one or more wireless networks, such as a cellular network (e.g., 4G, LTE), a WiFi network, a local area network, any other network, or any combination thereof. In some embodiments, the wireless connection permits the controller 118 to be located remotely from the optical interrogator 101.

Controller 118 includes a processor 116 and non-transitory computer-readable storage medium 120, as illustrated in FIG. 1. In an embodiment, the non-transitory computer-readable storage medium 120 has stored thereon computer-readable program instructions that, upon execution by a processor 116, cause the processor 116 to perform one or more operations, as discussed further herein.

Figure 2:
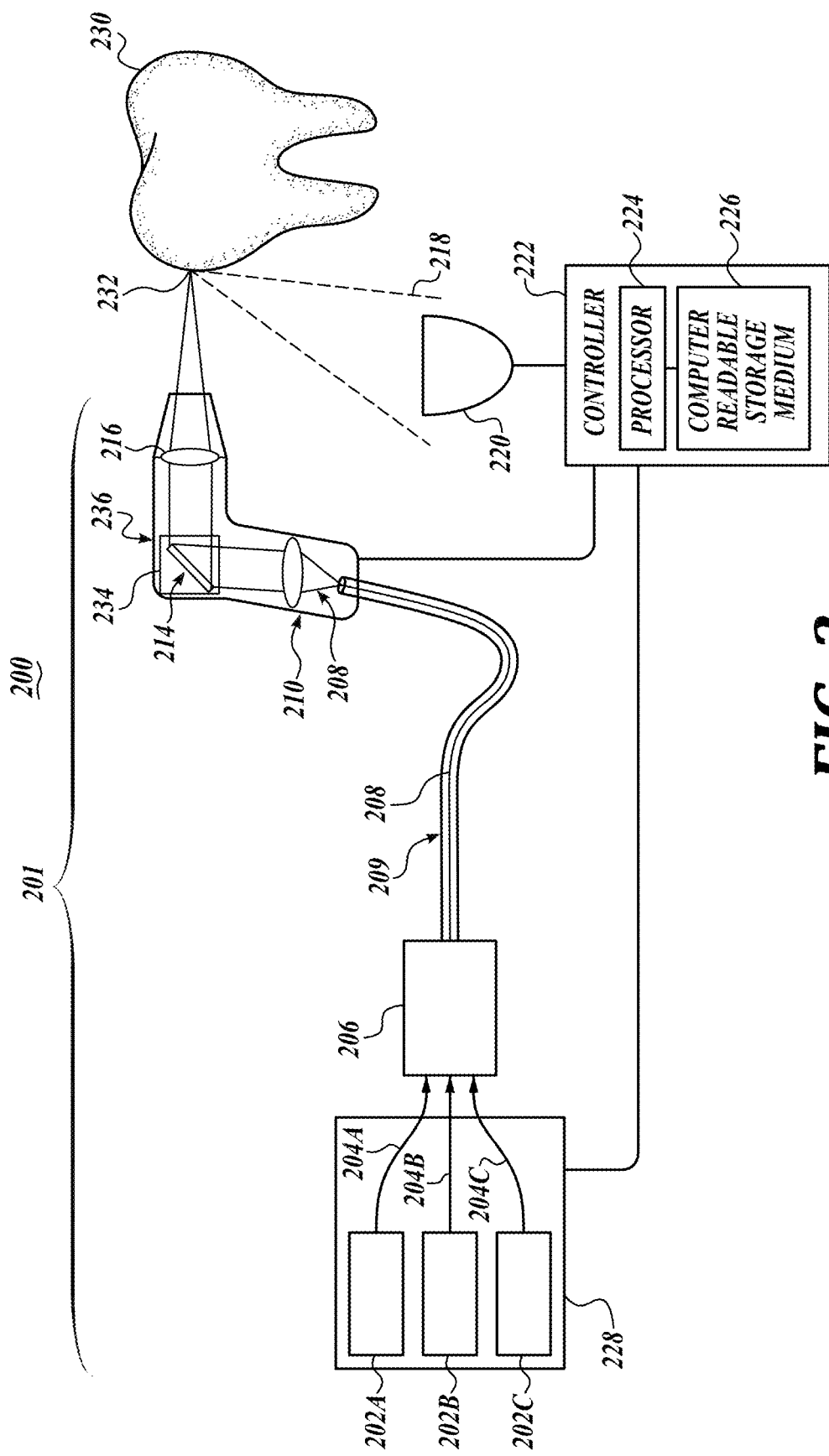
FIG. 2 illustrates another system for detecting carious lesions, in accordance with an embodiment of the disclosure.

FIG. 2 illustrates another system 200 for detecting carious lesions, in accordance with an embodiment of the disclosure. System 200 includes optical interrogator 201 and controller 222 operatively coupled to optical interrogator 201. System 200 may be generally similar to system 100.

Optical interrogator 201 includes a laser light engine 228; wavelength division multiplexer 206; scanning mirror assembly 234, and single-pixel photodetector 220. Laser light engine 228 is shown to include a plurality of lasers 202A, 202B, and 202C configured to emit laser light 204A, 204B, and 204C, respectively. As illustrated, wavelength division multiplexer 206 is coupled with the laser light engine 228 to combine at least a portion of the laser light 204A, 204B, and 204C emitted by the plurality of lasers 202A, 202B, and 202C to provide a combined light beam 208. Combined light beam 208 is directed by optical fiber 209 to scanning mirror assembly 234 to emit the combined light beam 208 onto tooth 230.

Scanning mirror assembly 234 is positioned to reflect the combined light beam 208. In the illustrated embodiment, scanning mirror assembly 234 includes a micro-electromechanical system 214 for selectively altering an orientation of the scanning mirror assembly 234.

The scanning mirror assembly 234 may also be an accousto-optical deflector positioned to selectively deflect the combined light beam 208 onto one or more portions of the tooth 230. The scanning mirror assembly 234 may also be an opto-electric scanner positioned to selectively deflect the combined light beam 208 onto one or more portions of the tooth 230. In an embodiment, the opto-electric scanner is a KTa1-xNbxO3 (KTN) scanner. Solid-state scanners, such as acousto-optic and opto-electric scanners, often scan at higher speeds than, for example, mechanical scanners having moving parts. Such higher scan speeds may be advantageous when used in conjunction with, for example, a hand-held probe, such as hand-held probe 236. When a hand-held probe 236 including a scanning mirror assembly 234 is held by a hand of a user, vibrations from the hand, for example, may be transferred to the probe 236, thereby altering an orientation of the combined light beam 208 emitted from the probe 236 toward the tooth 230. By scanning the combined light beam 208 over portions of the tooth 230 with a solid-state scanning assembly, an orientation of the probe 236 is likely to have changed less, if at all, during a scanning process than if the scanning mirror assembly 234 were scanned at a slower rate with, for example, a mechanical scanning assembly. Accordingly, a solid-state scanning assembly may provide a higher-fidelity representation of a tooth 230 than a mechanical scanning assembly, particularly when used as part of a hand-held-probe 236.

Optical interrogator 201 is shown to include a collimating lens 210 positioned to collimate the combined light beam 208. In an embodiment, the collimating lens 210 consists of a single lens. In an embodiment, the collimating lens 210 is a compound lens comprising two or more single lenses. In the illustrated embodiment, collimating lens 210 collimates the combined light beam 208 impinging upon the scanning mirror assembly 234.

Optical interrogator 201 includes a scan lens 216 positioned to focus the combined light beam 208 on a portion 232 of the tooth 230. In an embodiment, the scan lens 216 includes a single lens. This is in contrast to a compound lens including two or more lenses. In an embodiment, the scan lens 216 is a compound lens comprising two or more single lenses. Scan lens 216 is positioned to focus at least a portion of the combined light beam 208 reflected off of the scanning mirror assembly 234 onto the portion 232 of the tooth 230. In this regard, the system 200 is configured to focus the combined light beam 208 onto a smaller portion 232 of the tooth 230 than a system that merely reflects the combined light beam 208 onto a portion of the tooth 230. In this regard, system 200 is configured to interrogate a smaller portion 232 of the tooth 230 at a given time and providing a more-detailed survey of the tooth 230.

In an embodiment, portions of the optical interrogator 201, including the scanning mirror assembly 234, are disposed within a probe 236 shaped to be held and manipulated by a hand of a person (not shown). In this regard, a user can direct the combined light beam 208 emitted from the probe 236 onto, for example, a particular tooth for inspection. In the illustrated embodiment, the scanning mirror assembly 234, including the micro-electromechanical system 214; the collimating mirror 210; and the scan lens 216 are disposed within the probe 236, as illustrated in FIG. 2.

Optical interrogator 201 includes single-pixel photodetector 220 configured generate one or more signals responsive to infrared light absorbed by the single-pixel photodetector 220. In the illustrated embodiment, a portion of the scattered light 218 scattered off of the portion 232 of the tooth 230 impinges upon and is absorbed by the single-pixel photodetector 220.

System 200 further includes controller 222 operatively coupled to optical interrogator 201. In an embodiment, controller 22 includes a processor 224 and computer-readable storage medium 226. In an embodiment, controller 222 includes logic that, upon execution by the controller 222, causes the system 200 to perform one or more operations. In an embodiment, the operations include one or more of the operations described herein with respect to FIG. 1.

In the illustrated embodiment, the controller 222 is operatively coupled to laser light engine 228; probe 236 including the scanning mirror assembly 234; and single-pixel photodetector 220. Further, in an embodiment, the operations include one or more of: causing the laser light engine 228 to emit laser light 204A, 204B, and 204C having wavelengths in a range of about 900 nm to about 1,700 nm; selectively directing the combined light beam 208 over different portions of the tooth 230, such as portion 232, with the scanning mirror assembly 234; and correlating scattered light signals generated by the single-pixel photodetector 220 in response to the scattered light 218 and the portion 232 of the tooth 230.

Figure 3:
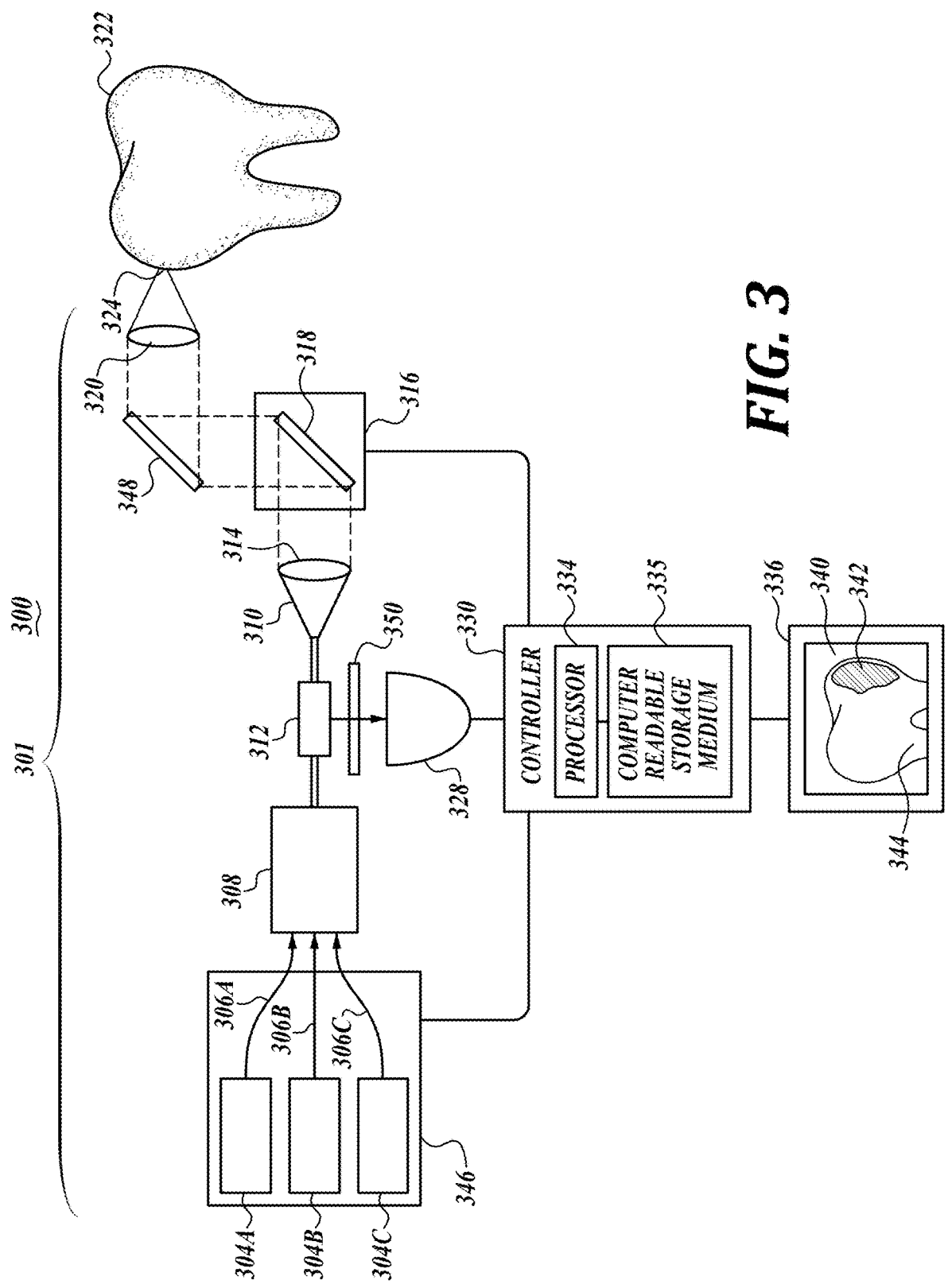
FIG. 3 illustrates another system for detecting carious lesions, in accordance with an embodiment of the disclosure.

FIG. 3 illustrates another system 300 for detecting carious lesions, in accordance with an embodiment of the disclosure. System 300 includes optical interrogator 301 and controller 330 operatively coupled to the optical interrogator 301. In an embodiment, system 300 is generally similar to one or more of systems 100 and 200.

Optical interrogator 301 includes laser light engine 346, wavelength division multiplexer 308 coupled with the laser light engine 346, scanning mirror assembly 316, double-clad optical fiber coupler 312, collimating lens 314, scan lens 320, mirror 348, a polarizer 350, and single-pixel photodetector 328. Laser light engine 346 includes a plurality of lasers 304A, 304B, and 304C configured to emit laser light 306A, 306B, and 306C, respectively. Wavelength division multiplexer 308 is coupled with the laser light engine 346 to combine at least a portion of the laser light 306A, 306B, and 306C emitted by the plurality of lasers 304A, 304B, and 304C to provide a combined light beam 310. As shown, scanning mirror assembly 316 includes micro-electromechanical system 318 for selectively altering an orientation of the scanning mirror assembly 316 to direct combined light beam 310.

As above, optical interrogator 301 includes double-clad optical fiber coupler 312 positioned to direct the combined light beam 310 to the scanning mirror assembly 316 and to direct the scattered light scattered off of the portion 324 of the tooth 322 to the single-pixel photodetector 328. As shown in FIG. 3, double-clad optical fiber coupler 312 in positioned to accept the combined light beam 310 emitted from the wavelength division multiplexer 308 and direct it through collimating lens 314 and eventually to the scanning mirror assembly 316. Further, as also shown in FIG. 3, the double-clad optical fiber coupler 312 is positioned to accept scattered light and direct the scattered light back through the portions of the optical interrogator 301, including scan lens 320, mirror 348, scanning mirror assembly 316, and collimating lens 314. The scattered light accepted by the double-clad optical fiber coupler 312 is directed to the single-pixel photodetector 328.

System 300 includes a polarizer 346 positioned between the double-clad optical fiber coupler 312 and the single-pixel photodetector 328 to polarize the scattered light accepted by the double-clad optical fiber coupler 312 and directed to the single-pixel photodetector 328. In an embodiment, the double-clad optical fiber coupler 312 is a polarization-maintaining optical fiber coupler 312. In this regard, system 300 is capable of acquiring a polarized and cross-polarized image of the tooth 322.

System 300 includes controller 330. In the illustrated embodiment, controller 330 includes a processor 334 and computer-readable storage medium 335. In an embodiment, controller 330 includes logic that, upon execution by the controller 330, causes the system 300 to perform one or more operations. In an embodiment, the operations include one or more operations described further herein with respect to FIGS. 1 and 2.

System 300 is shown to include output 336. In an embodiment, controller 330 includes logic that, upon execution by the controller 330, causes the system 300 to generate, with the output 336, one or more carious lesion signals indicative of a suspected carious lesion responsive to one or more signals generated by the single-pixel photodetector 328 above a predetermined level. In an embodiment, the predetermined level is a level that generally separates carious lesion signals and signals indicative of areas of intact enamel. In an embodiment, the one or more carious lesion signals include one or more of a visual, audio, haptic, or a tactile representation of a suspected carious lesion. In an embodiment, the operations include displaying with the output 336 an image 340 representative of the tooth 322 and an area 342 on the tooth 322 suspected of having a carious lesion. In an embodiment, the operations include displaying with the output 336 an image 340 representative of the tooth 322 and an area 342 on the tooth 322 suspected of having a carious lesion and an area 344 on the tooth suspected of having intact enamel.

Figure 4:
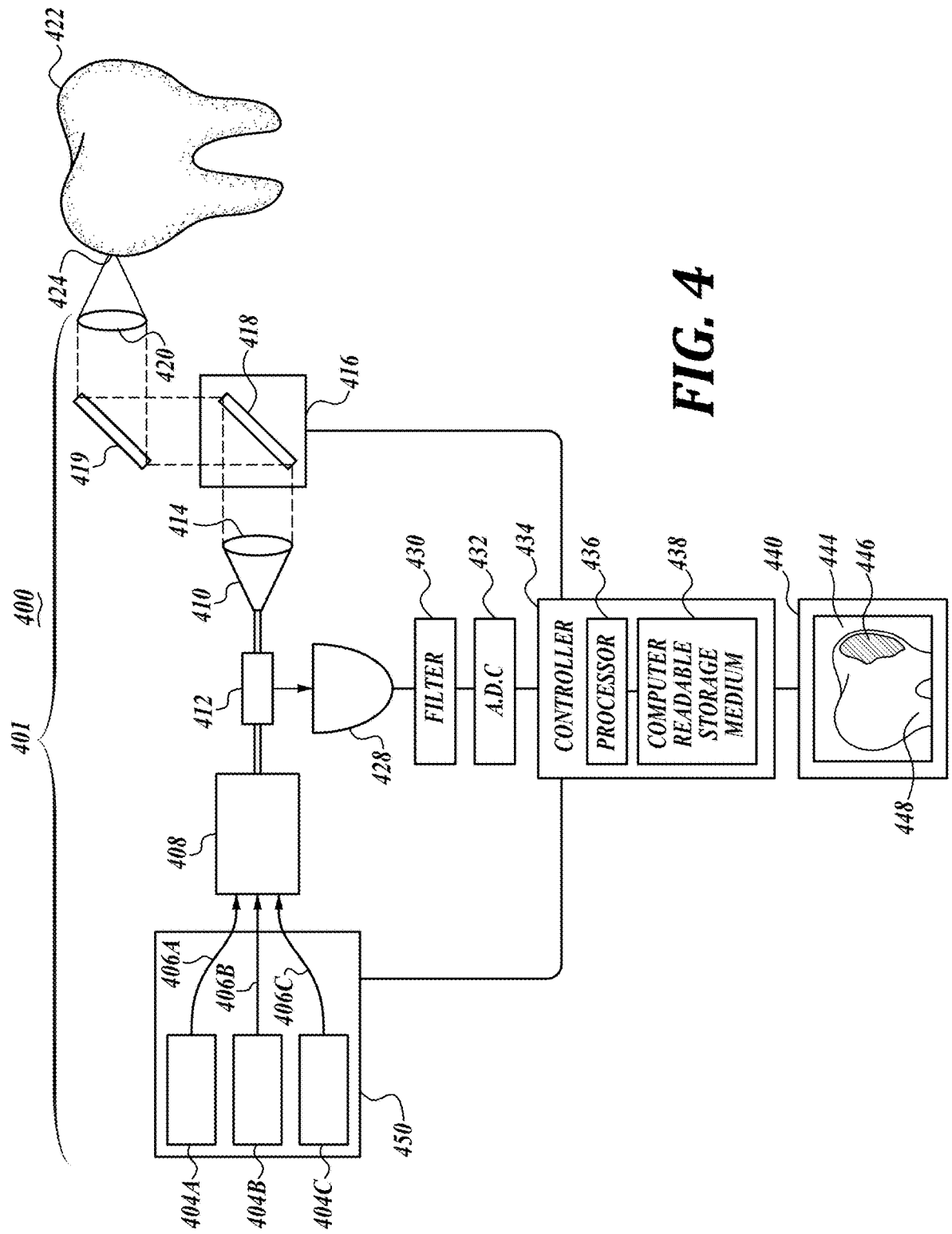
FIG. 4 illustrates another system for detecting carious lesions, in accordance with an embodiment of the disclosure.

FIG. 4 illustrates another system 400 for detecting carious lesions, in accordance with an embodiment of the disclosure. System 400 includes optical interrogator 401 and controller 434 operatively coupled to optical interrogator 401. In an embodiment, system 400 is generally similar to one or more of systems 100, 200, and 300.

In the illustrated embodiment, optical interrogator 401 includes laser light engine 450 including lasers 404A, 404B, and 404C; wavelength division multiplexer 408 coupled with the laser light engine 450 to combine at least a portion of the laser light 406A, 406B, and 406C emitted by lasers 404A, 404B, and 404C, respectively, to provide a combined light beam 410; collimating lens 414; scanning mirror assembly 416 including micro-electromechanical system 418 for selectively altering an orientation of the scanning mirror assembly 416; mirror 419; scan lens 420 shaped to focus combined light beam 410 to a portion 424 of tooth 422; double-clad optical fiber coupler 412; single-pixel photodetector 428; filter 430; and analog-to-digital converter (ADC) 432.

As above, optical interrogator 401 includes filter 430. In an embodiment, filter 430 is configured to filter wavelengths of light that are outside the range of about 900 nm to about 1,700 nm from being absorbed by single-pixel photodetector 428. In this regard, the filter 430 is configured to filter out light that does not include, for example, scattered light emitted by laser light engine 450 and scattered off of tooth 422. In an embodiment, the filter 430 is an optical filter. In the illustrated embodiment, filter 430 is an electronic filter configured to remove from signals generated by the single-pixel photodetector 428 that not are responsive to scattered light absorbed by the single-pixel photodetector 428. In an embodiment, the filter 430 is a band-pass filter. In an embodiment, the filter 430 is a low-pass filter.

Optical interrogator 401 includes ADC 432 operatively coupled to the single-pixel photodetector 428. In an embodiment, the scattered light signals generated by single-pixel photodetector 428 include one or more analog signals and, in an embodiment, the ADC 432 is configured to generate one or more digital signals in response to the one or more analog signals. In this regard, the ADC 432 is configured to provide the controller 434 with one or more digital signals responsive to scattered light absorbed by the single-pixel photodetector 428.

As shown, controller 434 includes processor 436 operatively coupled to computer-readable storage medium 438. In an embodiment, the non-transitory computer-readable storage medium 438 has stored thereon computer-readable program instructions that, upon execution by a processor 436, cause the system 400 to perform one or more operations, as discussed further herein.

System 400 is shown to include output 440. In an embodiment, controller 434 includes logic that, upon execution by the controller 434, causes the system 400 to generate, with the output 440, one or more carious lesion signals indicative of a suspected carious lesion responsive to one or more signals generated by the single-pixel photodetector 428 above a predetermined level. In an embodiment, the predetermined level is a level that generally separates carious lesion signals and signals indicative of areas of intact enamel. In an embodiment, the one or more carious lesion signals include one or more of a visual, audio, haptic, or a tactile representation of a suspected carious lesion. In an embodiment, the operations include displaying with the output 440 includes an image 444 representative of the tooth 422 and an area 446 on the tooth 422 suspected of having a carious lesion. In an embodiment, the operations include displaying with the output 440 an image 444 representative of the tooth 422 and an area 446 on the tooth 422 suspected of having a carious lesion and an area 448 on the tooth suspected of having intact enamel.

In another aspect, the present disclosure provides a method of detecting a carious lesion on a tooth. In an embodiment, the method includes emitting, from a plurality of lasers, laser light having wavelengths in a range of about 900 nm to about 1,700 nm; combining the laser light into a combined light beam with a wavelength division multiplexer; selectively directing the combined light beam with a scanning mirror assembly over different portions of the tooth to provide scattered light; generating scattered light signals with a single-pixel photodetector in response to the scattered light; and generating one or more carious lesion signals indicative of a suspected carious lesion when the scattered light signals are above a predetermined level.

In an embodiment, the method includes emitting from a plurality of lasers laser light having wavelengths in a range of about 900 nm to about 1,700 nm. In an embodiment, the method includes emitting from a plurality of lasers laser light having wavelengths in a range of about 1,400 nm to about 1,700 nm. As discussed further herein with respect to FIGS. 1 and 5C, light having wavelengths between about 900 nm and about 1,700 nm, and, particularly, between about 1,400 nm and about 1,700 nm, provides greater contrast between areas of intact enamel and carious lesions. In an embodiment, emitting from a plurality of lasers, laser light having wavelengths in a range of about 900 nm to about 1,700 nm includes emitting laser light from a laser light engine including a plurality of lasers. In an embodiment, the laser light engine is a laser light engine chosen from laser light engines 105, 228, 346, and 428.

In an embodiment, the method includes combining the laser light into a combined light beam with a wavelength division multiplexer. In this regard, the wavelength division multiplexer provides a single combined light beam for later manipulation and analysis. In an embodiment, the wavelength division multiplexer is a wavelength division multiplexer chosen from wavelength division multiplexers 104, 206, 308, and 408.

In an embodiment, the method includes selectively directing the combined light beam with a scanning assembly over different portions of the tooth. In an embodiment, the scanning assembly is a scanning mirror assembly including a micro-electromechanical system, and wherein selectively directing the combined light beam onto a portion of the tooth with a scanning mirror assembly includes selectively altering an orientation of the scanning mirror assembly with the micro-electromechanical system. In an embodiment, the scanning mirror assembly is chosen from scanning mirror assemblies 108, 234, 316, and 416 as discussed further herein. In an embodiment, selectively directing the combined light beam with a scanning mirror assembly over different portions of the tooth includes rastering or otherwise systematically directing the combined light beam onto the portions of the tooth.

In an embodiment, the method includes generating one or more signals with the single-pixel photodetector in response to the scattered light. In an embodiment, the method further includes correlating the scattered light signals to the portion of the tooth. As discussed further herein, in this regard the methods of the present disclosure are suitable to generate a map or other data structure representative of the tooth and any carious lesions disposed thereon.

In an embodiment, the method includes generating a carious lesion signal indicative of a suspected carious lesion when the scattered light signals are above a predetermined level. As discussed further herein, in an embodiment, the predetermined level is generally a level that separates scattered light signals indicative of carious lesions and scattered light signals indicative of areas of intact enamel.

FIG. 5A is an optical image of two teeth 502A and 502B. FIG. 5B is a short-wave infrared light image of the teeth 502A and 502B in FIG. 5A taken at 1310 nm, represented here as 503A and 503B, respectively.

Figure 5C:
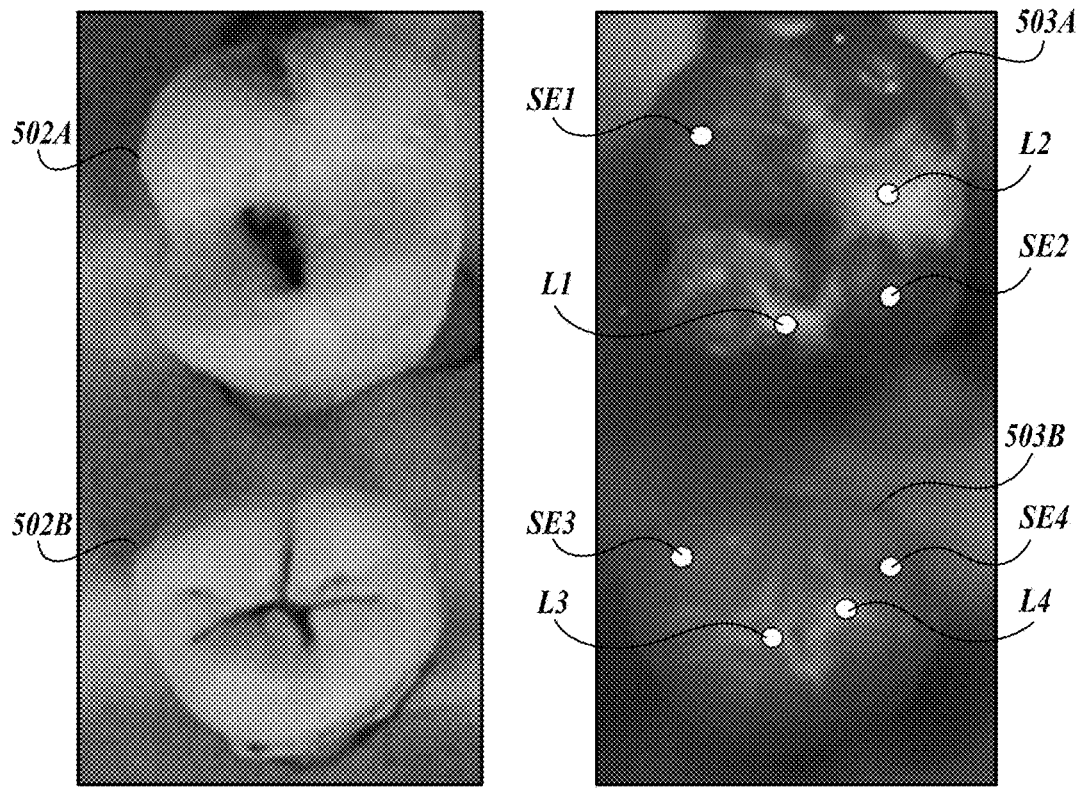
FIG. 5C graphically illustrates diffuse reflectance off of portions of the teeth of FIG. 5A as a function of wavelength.
Figure 5C:
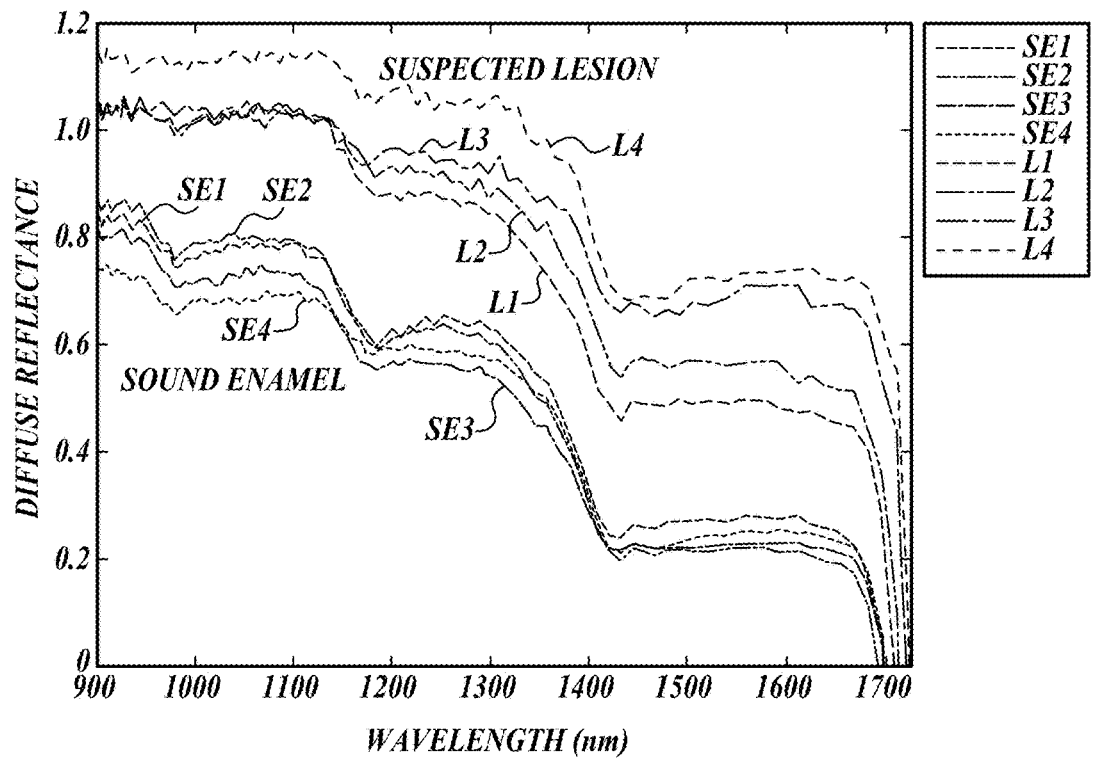

As shown in FIG. 5B, areas L1, L2, L3, and L4 suspected of having carious lesions are lighter than areas SE1, SE2, SE3, and SE4 suspected of having areas of intact enamel, due to the increased scattering of SWIR light off of areas including carious lesions. FIG. 5C graphically illustrates diffuse reflectance off of areas L1, L2, L3, and L4 and areas SE1, SE2, SE3, and SE4 as a function of wavelength. As illustrated, the light scattered off of teeth 502A and 502B is SWIR light between about 900 nm and about 1,700 nm.

In an embodiment, one or more of the plurality of lasers emit laser light having a different emission spectrum than other lasers in the plurality of lasers. In this regard, in an embodiment, the laser light emitted by the laser light engine is configured to provide enhanced contrast between carious lesions and areas of intact enamel.

In an embodiment, the relative emission intensity of each of the plurality of lasers is determined by a machine learning process. In an embodiment, the machine learning process includes generating a training data set; and training a linear support vector machine on the training data set to generate a classifying vector having coefficients, wherein the coefficients define at least in part the relative intensity of the plurality of lasers.

In an embodiment, generating the training data set includes annotating the teeth by one or more dental care professionals, such as one or more dentists and/or one or more dental hygienists. In annotating the teeth, the one or more dental care professionals note one or more areas suspected of having carious lesions and one or more areas having intact enamel. Annotating can include visual inspection of one or more teeth by one or more dental care professionals.

Figure 6A:
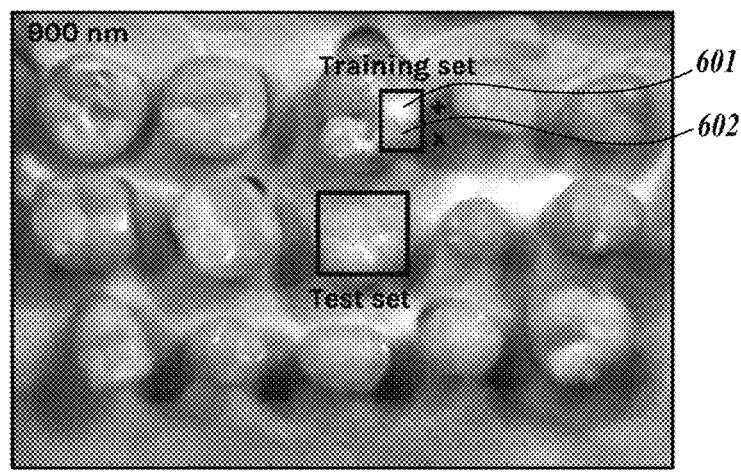
FIG. 6A is a short-wave infrared light image of teeth including carious lesions and areas of intact enamel.

FIG. 6A is a short-wave infrared light image of teeth, including carious lesions and areas of intact enamel. FIG. 6A shows an area 601 suspected of including one or more carious lesions and an area 602 having intact enamel that has been annotated by one or more dental care professionals.

In an embodiment, the process of generating a training data set includes generating hyperspectral reflectance spectra from one or more carious lesions and one or more areas of intact enamel. Generating hyperspectral reflectance spectra can include directing the output of a tunable laser onto one or more areas suspected of having carious lesions and one or more areas having intact enamel. In an embodiment, the laser is a tunable optical parametric oscillator (OPO). In an embodiment, the laser is a super-continuum laser source with a tunable filter.

Generating hyperspectral reflectance spectra can include changing the wavelength of a light source, such as with a tunable laser, and at each wavelength capturing an image of, for example, one or more areas suspected of having carious lesions and one or more areas having intact enamel. In this way, for each of the one or more areas suspected of having carious lesions and one or more areas having intact enamel, a hyperspectral reflectance data cube is collected.

In generating training data, light scattered off the one or more areas suspected of having carious lesions and one or more areas having intact enamel is directed to an infrared-sensitive sensor, which generates one or more signals responsive to the reflected light. In an embodiment, light scattered off of the one or more areas suspected of having carious lesions and one or more areas having intact enamel is collected by a lens and imaged onto a multi-pixel InGaAs camera. In an embodiment, light scattered off of the one or more areas suspected of having carious lesions and one or more areas having intact enamel is directed to a system as described further herein.

Figure 6B:
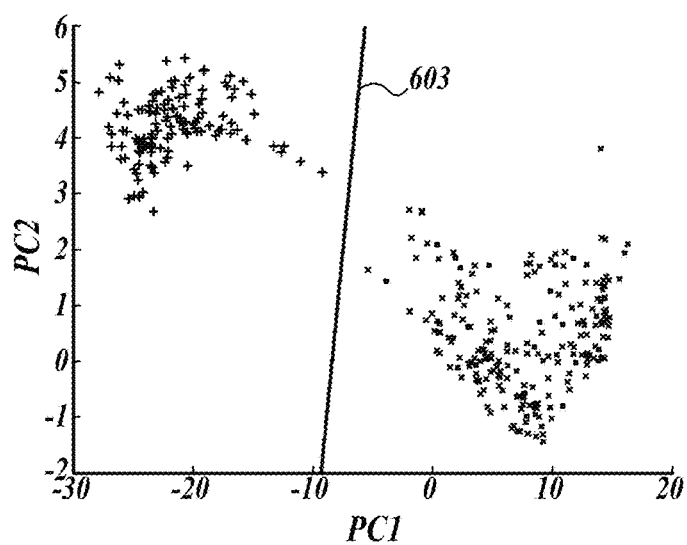
FIG. 6B graphically illustrates hyperspectral reflectance data represented in reduced dimensions using principal component analysis and a classifying vector, in accordance with an embodiment of the disclosure.

The hyperspectral reflectance spectrum from each region of the specimen can thus be labeled as coming from sound (no lesions) or demineralized (with lesion) enamel. In an embodiment, such data is collected from many tooth samples. In an embodiment, this data is included in the training data set. FIG. 6B graphically illustrates hyperspectral reflectance data represented in reduced dimensions using principal component analysis and a classifying vector, in accordance with an embodiment of the disclosure. The hyperspectral reflectance data illustrated in FIG. 6B includes reflectance from carious lesions, "+", and areas of intact enamel, "x". In an embodiment, a linear support vector machine (SVM) is trained on the hyperspectral dataset to generate the classifying vector, such as classifying vector 603 illustrated in FIG. 6B. In an embodiment, the features of the classifying vector 603 are the wavelength channels in the reflectance spectrum. The coefficients of the classifying vector 603, i.e. the hyperplane that divides the positive (+) and negative (x) examples, are noted. These coefficients give the relative intensities of the laser sources in the laser light engine which provides enhanced contrast between sound and demineralized enamel. In an embodiment, wavelengths corresponding to large classifying-vector coefficients are chosen for the lasers in the laser light engine. A plurality of inexpensive visible lasers can be used for calibration and/or color rendering.

Figure 6C:
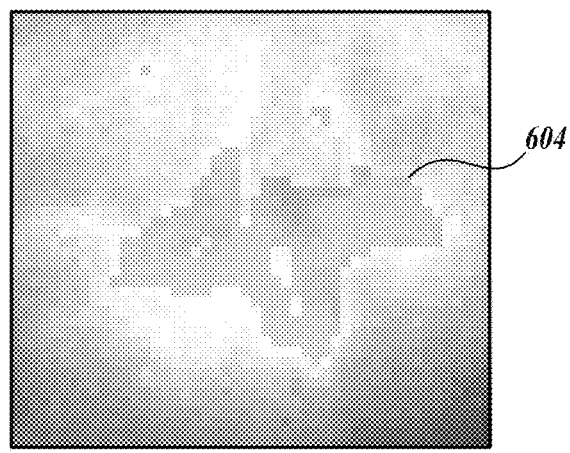
FIG. 6C is a composite image including an image representative of a tooth and an area suspected of having a carious lesion, in accordance with an embodiment of the disclosure.

FIG. 6C is a composite image including an image representative of the test tooth of FIG. 6A and an area on the tooth suspected of having a carious lesion, in accordance with an embodiment of the disclosure. As illustrated, the image includes area 604 suspected of having a carious lesion is highlighted and superimposed over the image of the tooth. In this regard, the method highlights for a dental care professional an area suspected of having a carious lesion, for example, for future treatment of the carious lesion.

Figure 7A:
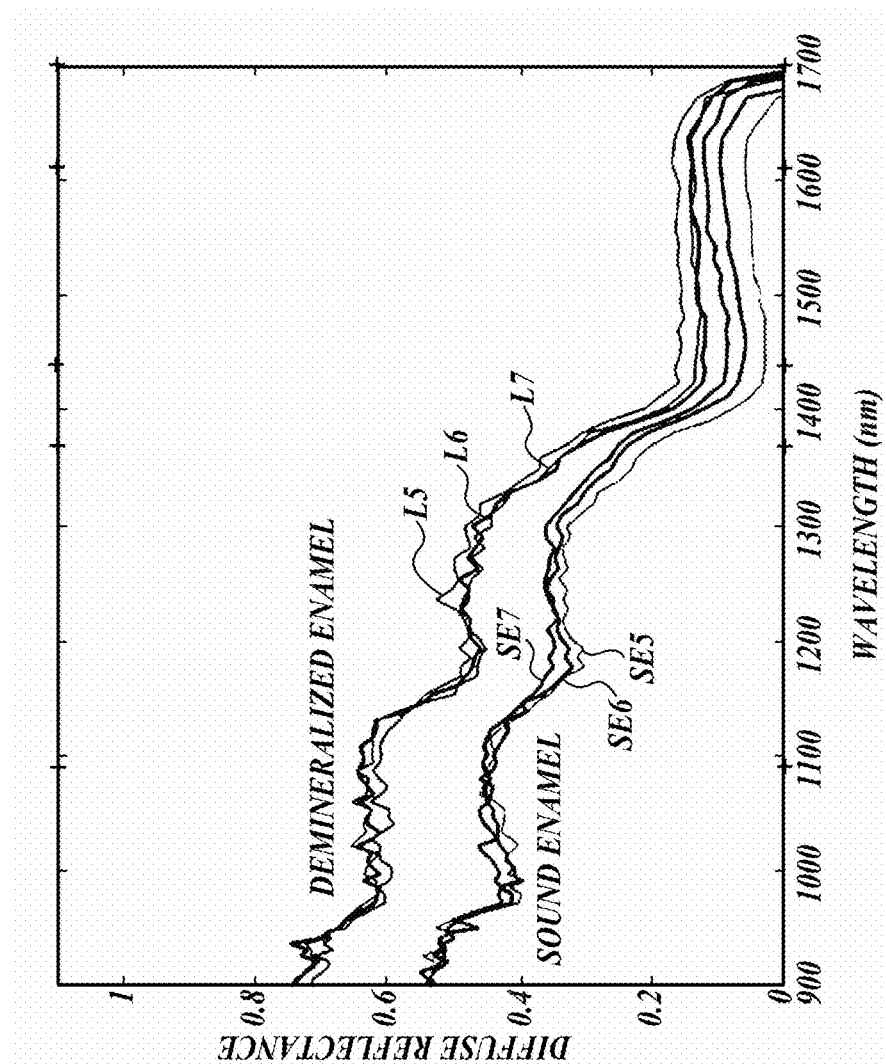
FIG. 7A graphically illustrates diffuse reflectance off of areas of a partially demineralized tooth as a function of wavelength, in accordance with an embodiment of the disclosure.
Figure 7B:
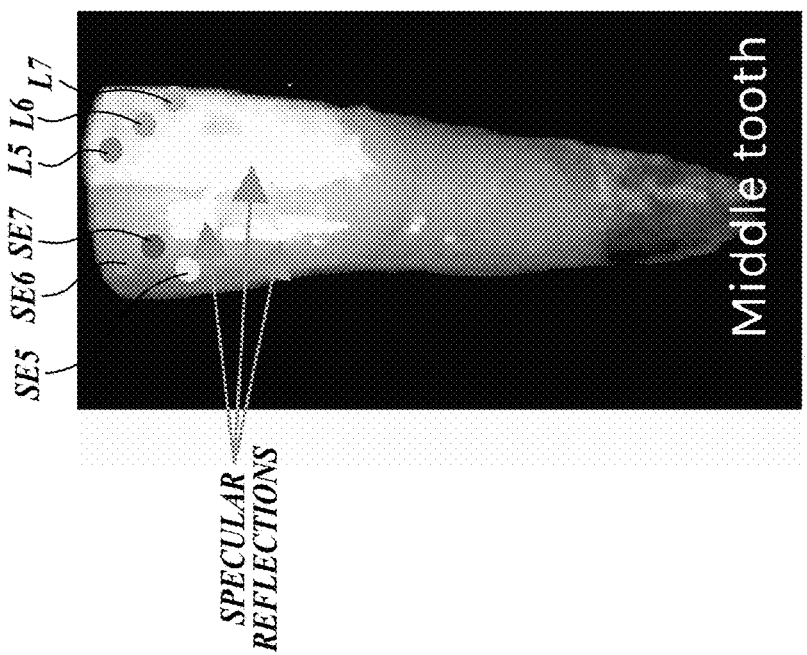
FIG. 7B is a short-wave infrared light image of the partially demineralized tooth of FIG. 7A, in accordance with an embodiment of the disclosure.

To confirm the annotations of dental care professionals, teeth were partially demineralized and examined as described herein. Teeth were masked with lacquer (clear nail polish) resistant to demineralization and then soaked in a demineralization solution for 24-30 minutes. The demineralization solution included 8.3 mmol/L $CaCl_2$, 8.3 mmol/L $NaH2PO4$, 50 mmol/L acetic acid, NaOH to pH 4.0. FIG. 7A graphically illustrates diffuse reflectance off of areas of a partially demineralized tooth as a function of wavelength, in accordance with an embodiment of the disclosure. FIG. 7B is a short-wave infrared light image of the partially demineralized tooth of FIG. 7A, in accordance with an embodiment of the disclosure. As illustrated, the areas of demineralized enamel L5, L6, and L7 have higher diffuse reflectance than the areas of intact enamel SE5, SE6, and SE7 over a number of wavelengths between 900 nm and 1,700 nm, thus confirming the annotations by dental care professionals.

The order in which some or all of the processes appear in each process should not be deemed limiting. Rather, one of ordinary skill in the art having the benefit of the present disclosure will understand that some of the process blocks may be executed in a variety of orders not illustrated, or even in parallel.

The operations explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit (ASIC) or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

The embodiments of the invention in which an exclusive property or privilege is claimed are defined as follows:

1. A system for detecting carious lesions on a tooth, the system comprising:
    an optical interrogator including:
    a plurality of lasers for emitting laser light;
    a wavelength division multiplexer coupled with the plurality of lasers to combine the laser light emitted by the plurality of lasers to provide a combined light beam;
    a probe shaped to be held and manipulated by a hand of a person housing a scanning mirror assembly including a solid-state scanning assembly positioned to reflect the combined light beam; and
    a single-pixel indium-gallium-arsenide (InGaAs) photodetector having a single InGaAs photodiode;
    a double-clad optical fiber coupler positioned to direct the combined light beam to the scanning mirror assembly and to direct scattered light to the single-pixel photodetector; and a controller operatively coupled to the optical interrogator including logic that, upon execution by the controller, causes the system to perform operations including:
causing the plurality of lasers to emit the laser light having wavelengths in a range of about 900 nm to about 1,700 nm;
selectively altering an orientation of the scanning mirror assembly thereby directing the combined light beam over different portions of the tooth with the scanning mirror assembly to the provide scattered light; and
correlating scattered light signals generated by the single-pixel photodetector in response to the scattered light with the portion of the tooth.

2. The system of claim 1, wherein one or more of the plurality of lasers emit laser light having a different emission spectrum than other lasers of the plurality of lasers.

3. The system of claim 1, wherein the optical interrogator further includes an output, and wherein the operations further include generating, with the output, one or more carious lesion signals indicative of a suspected carious lesion responsive to one or more scattered light signals above a predetermined level.

4. The system of claim 3, wherein the output is configured to display an image representative of the tooth and an area on the tooth suspected of having a carious lesion.

5. The system of claim 1, wherein the optical interrogator further includes a collimating lens positioned to collimate the combined light beam.

6. The system of claim 1, wherein the optical interrogator further includes a scan lens positioned to focus the combined light beam on the portion of the tooth.

7. The system of claim 1, wherein the optical interrogator further includes a filter configured to filter wavelengths of light in the scattered light that are outside the range of about 900 nm to about 1,700 nm.

8. The system of claim 1, wherein the scattered light signals include one or more analog signals, and wherein the optical interrogator further comprises a converter configured to generate digital signals in response to the one or more analog signals for receipt by the controller.

9. The system of claim 1, wherein one or more of the plurality of lasers is configured to emit laser light having wavelengths in a range of about 1,400 nm to about 1,700 nm.

10. A method of detecting a carious lesion on a tooth comprising:
emitting, from a plurality of lasers, laser light having wavelengths in a range of about 900 nm to about 1,700 nm;
combining the laser light emitted by the plurality of lasers into a combined light beam with a wavelength division multiplexer;
selectively directing the combined light beam with a scanning mirror assembly optically coupled to a double-clad optical fiber coupler and including a solid-state scanning assembly over different portions of the tooth to provide scattered light including selectively altering an orientation of the scanning mirror assembly with the solid-state scanning assembly, wherein the scanning mirror assembly is disposed within a probe shaped to be held and manipulated by a hand of a person;
generating scattered light signals with a single-pixel InGaAs photodetector having a single InGaAs photodiode in response to the scattered light received from the double-clad optical fiber coupler; and
generating one or more carious lesion signals indicative of a suspected carious lesion when the scattered light signals are above a predetermined level.

11. The method of claim 10, wherein one or more of the plurality of lasers emit laser light having a different emission spectrum than other lasers in the plurality of lasers.

12. The method of claim 11, wherein the relative emission intensity of each of the plurality of lasers is determined by a machine learning process comprising:
generating a training data set by a process including:
annotating, by one or more dental care professionals, a plurality of carious lesions and a plurality of areas of intact tooth enamel; and
generating hyperspectral reflectance spectra from the plurality of carious lesions and the plurality of areas of intact enamel to provide the training data set; and
training a linear support vector machine on the training data set to generate a classifying vector having coefficients, wherein the coefficients define at least in part the relative emission intensity of the plurality of lasers.

13. The method of claim 10, further comprising correlating the scattered light signals and the portions of the tooth.

14. The method of claim 10, further comprising displaying an image representative of the tooth and an area on the tooth suspected of having a carious lesion.

15. A system for detecting carious lesions on a tooth, the system comprising:
an optical interrogator including:
a plurality of lasers for emitting laser light;
a wavelength division multiplexer coupled with the plurality of lasers to combine the laser light emitted by the plurality of lasers to provide a combined light beam;
a probe shaped to be held and manipulated by a hand of a person housing a scanning mirror assembly including a solid-state scanning assembly positioned to reflect the combined light beam;
a single-pixel photodetector;
a double-clad optical fiber coupler positioned to direct the combined light beam to the scanning mirror assembly and to direct the scattered light to the single-pixel photodetector; and
a controller operatively coupled to the optical interrogator including logic that, upon execution by the controller, causes the system to perform operations including:
causing the plurality of lasers to emit the laser light having wavelengths in a range of about 900 nm to about 1,700 nm;
selectively altering an orientation of the scanning mirror assembly thereby directing the combined light beam over different portions of the tooth with the scanning mirror assembly to provide scattered light; and
correlating scattered light signals generated by the single-pixel photodetector in response to the scattered light with the portion of the tooth.

16. The system of claim 1, wherein the solid-state scanning assembly is selected from an acousto-optic scanner and an opto-electric scanner.

* * * * *